(12) United States Patent
List et al.

(10) Patent No.: US 10,278,631 B2
(45) Date of Patent: *May 7, 2019

(54) PUNCTURING SYSTEM

(75) Inventors: Hans List, Hesseneck-Kailbach (DE); Christian Hoerauf, Oftersheim (DE); Frank Deck, Niederkirchen (DE); Thomas Weiss, Mannheim (DE); Michael Keil, Ludwigshafen (DE); Guenther Schmelzeisen-Redeker, Lorsch (DE); Heinrich Fruhstorfer, Marburg (DE); Hans-Peter Haar, Wiesloch (DE); Uwe Kraemer, Ilvesheim (DE); Joachim Hoenes, Zwingenberg (DE); Karl Miltner, Frankenthal (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 596 days.

This patent is subject to a terminal disclaimer.

(21) Appl. No.: 13/619,459

(22) Filed: Sep. 14, 2012

(65) Prior Publication Data

US 2013/0066356 A1 Mar. 14, 2013

Related U.S. Application Data

(63) Continuation of application No. 12/057,779, filed on Mar. 28, 2008, now Pat. No. 8,287,467, which is a (Continued)

(30) Foreign Application Priority Data

Oct. 8, 2005 (EP) ..................... 05021983

(51) Int. Cl.
*A61B 5/15* (2006.01)
*A61B 5/151* (2006.01)
*A61B 5/145* (2006.01)

(52) U.S. Cl.
CPC ...... *A61B 5/1519* (2013.01); *A61B 5/150022* (2013.01); *A61B 5/150068* (2013.01);
(Continued)

(58) Field of Classification Search
None
See application file for complete search history.

(56) References Cited

U.S. PATENT DOCUMENTS 4,577,630 A 3/1986 Nitzsche et al.
5,035,704 A 7/1991 Lambert et al.
(Continued)

FOREIGN PATENT DOCUMENTS

DE 198 55 443 6/1999
DE 103 32 283 2/2005
(Continued)

*Primary Examiner* — Matthew Kremer
(74) *Attorney, Agent, or Firm* — Bose McKinney & Evans LLP (57) ABSTRACT

Disclosed is a puncturing system for generating a puncture wound for obtaining a sample of a body fluid, comprising a press-on part to be pressed onto a body part in which a puncture wound is to be generated, a trigger, by the actuation of which a user can trigger a puncturing motion of a puncturing element after the press-on part is pressed on, and a testing facility for determining at least one test parameter on which a sample-obtaining probability depends. A securing facility is also provided that, in a locked state, locks the trigger such that no puncturing motion can be triggered, and, in a triggering state, releases the trigger such that a puncturing motion can be triggered by actuation thereof, whereby the securing facility is transitioned from the locked state to the triggering state by the testing facility when the test parameter determined by the testing facility meets defined minimum requirements. A signaling facility is also provided for signaling a transition of the securing facility to the triggering state and/or for signaling that the securing facility (Continued)

is in the triggering state. Also disclosed is a method for preparing a puncturing system for generating a puncture wound.

16 Claims, 3 Drawing Sheets

Related U.S. Application Data continuation of application No. PCT/EP2006/009257, filed on Sep. 23, 2006.

(52) U.S. Cl.
CPC .... *A61B 5/15113* (2013.01); *A61B 5/150412* (2013.01); *A61B 5/150503* (2013.01); *A61B 5/150824* (2013.01); *A61B 5/150954* (2013.01); *A61B 5/14532* (2013.01)

(56) References Cited

U.S. PATENT DOCUMENTS

| | | | |
|---|---|---|---|
| 5,366,469 A | 11/1994 | Hans-Henning et al. | |
| 5,478,316 A * | 12/1995 | Bitdinger | A61M 5/2033 604/134 |
| 5,741,288 A | 4/1998 | Rife | |
| 5,871,494 A | 2/1999 | Simons et al. | |
| 5,879,311 A | 3/1999 | Duchon et al. | |
| 5,964,718 A * | 10/1999 | Duchon et al. | 600/583 |
| 5,971,911 A | 10/1999 | Wilk | |
| 6,589,260 B1 | 7/2003 | Schmelzeisen-Redeker et al. | |
| 6,706,159 B2 | 3/2004 | Moerman et al. | |
| 6,986,754 B2 | 1/2006 | Haar et al. | |
| 7,288,102 B2 | 10/2007 | Griffin et al. | |
| 7,291,159 B2 | 11/2007 | Schmelzeisen-Redeker et al. | |
| 8,043,318 B2 | 10/2011 | Schraga | |
| 8,147,425 B2 | 4/2012 | Nakamura et al. | |
| 8,287,467 B2 * | 10/2012 | List et al. | 600/583 |
| 2002/0169412 A1 | 11/2002 | Haar et al. | |
| 2002/0177787 A1 * | 11/2002 | Duchon et al. | 600/583 |
| 2003/0018300 A1 | 1/2003 | Duchon et al. | |
| 2003/0083686 A1 | 5/2003 | Freeman et al. | |
| 2003/0212344 A1 | 11/2003 | Yuzhakov et al. | |
| 2004/0030353 A1 | 2/2004 | Schmelzeisen-Redeker et al. | |
| 2004/0215224 A1 | 10/2004 | Sakata et al. | |
| 2004/0254599 A1 * | 12/2004 | Lipoma et al. | 606/181 |
| 2004/0260326 A1 * | 12/2004 | Lipoma | A61B 5/150022 606/182 |
| 2005/0038465 A1 | 2/2005 | Shraga | |
| 2005/0131342 A1 | 6/2005 | Haar et al. | |
| 2006/0173379 A1 | 8/2006 | Rasch-Menges et al. | |
| 2006/0224171 A1 * | 10/2006 | Sakata | A61B 5/15186 606/181 |
| 2007/0100365 A1 | 5/2007 | Deck | |
| 2008/0194987 A1 | 8/2008 | Boecker | |
| 2009/0036915 A1 * | 2/2009 | Karbowniczek et al. | 606/182 |
| 2009/0275860 A1 | 11/2009 | Nakamura et al. | |

FOREIGN PATENT DOCUMENTS

| | | | |
|---|---|---|---|
| DE | 10 2004 024 970 | 12/2005 | |
| EP | 0 565 819 | 10/1993 | |
| EP | 1 243 281 | 9/2002 | |
| EP | 1 360 933 | 11/2003 | |
| EP | 1 407 712 | 4/2004 | |
| JP | WO 2004082478 A1 * | 9/2004 | A61B 5/15186 |
| WO | WO 2001/072220 | 10/2001 | |
| WO | WO 2001/089383 | 11/2001 | |
| WO | WO 2002/100274 | 12/2002 | |
| WO | WO 2006067119 A2 * | 6/2006 | A61B 5/1411 |
| WO | WO 2006/109452 A1 | 10/2006 | |

\* cited by examiner

PUNCTURING SYSTEM

This application is a continuation of U.S. patent application Ser. No. 12/057,779, filed Mar. 28, 2008, now U.S. Pat. No. 8,287,467 which is a continuation application of International Application PCT/EP2006/009257, filed Sep. 23, 2006, which claims priority to EP 05 021 983.1, filed Oct. 8, 2005, all of which are hereby incorporated by reference in their entirety.

BACKGROUND

The invention relates to a puncturing system for generating a puncture wound for obtaining a sample of a body fluid. The body fluid is typically blood, but in some cases may be interstitial fluid. Reference shall be made hereinafter to blood as an example of body fluids, recognizing that fluids other than blood can be obtained from a puncture wound.

Puncturing systems (lancing devices) of this type usually consist of disposable puncturing elements that are designed for single use for puncturing the skin and a puncturing device having a drive for the puncturing motion of the puncturing element. The puncturing device of a puncturing system of this type has a press-on part to be pressed onto the body part in which a puncture wound is to be generated and a triggering means, by the actuation of which a user can trigger a puncturing motion of a puncturing element.

It is a consistent goal in the development of puncturing systems to generate with as little pain as possible a puncture wound from which a useful sample, i.e., a sufficient quantity of a body fluid, can be obtained. The depth of penetration is very important for both the sensation of pain and for obtaining the sample. In general, both the sensation of pain as well as the quantity of liquid that can be obtained from the puncture wound increase with increasing depth of puncturing. Puncturing devices are therefore required, on the one hand, to keep the depth of puncturing as small as possible, while on the other hand providing it to be as deep as necessary.

An important test parameter in this context is the pressure at which the press-on part is pressed onto a body part. If the pressure is too low, it is possible that the desired depth of puncturing will not be reached during a puncture and that a useful sample will not be obtained for this reason. In this case, the puncturing procedure must be repeated, which is extremely unpleasant for a user.

In order to reduce the likelihood of an unsuccessful puncture, it is known to provide a puncturing device having a pressure sensor, in which a puncturing motion is triggered automatically as soon as a pressure that exceeds a predetermined minimum pressure bears on the press-on part. Such devices are known, for example, from U.S. Pat. No. 5,879, 311.

A puncturing device having a built-in pressure sensor is also described in EP 1 360 933. However, a puncture is not triggered automatically by the pressure sensor in this puncturing device. Instead, the device only displays whether the pressure bearing on the press-on part is within one of three predetermined ranges (low, normal, and high). A puncturing motion is triggered by pressing a key on the device housing.

A puncturing device having a built-in pressure sensor is also known from EP 1 407 712. In this device, a negative pressure is generated after the device is placed against the skin such that the tissue is made to bulge into a device opening. The negative pressure generated is measured with the pressure sensor and compared to a stored threshold value. In this context, EP 1 407 712 mentions both the possibility of a puncturing motion being triggered automatically as soon as the negative pressure reaches a favorable value, as well as the possibility of a puncture being triggered by a user by closing a switch when it is displayed that the measured negative pressure has reached a predetermined threshold value.

It is desirable to devise a way in which the risk of an unsuccessful puncture that fails to obtain a useful sample can be reduced while at the same time keeping the convenience for the user as high as possible without increasing the sensation of pain due to the depth of puncturing being unnecessarily large.

SUMMARY OF THE INVENTION

Exemplary embodiments of the present invention provide a puncturing system for generating a puncture wound for obtaining a sample of a body fluid, comprising a press-on part to be pressed on a body part in which a puncture wound is to be generated, a triggering means by actuation of which a user can trigger a puncturing motion of a puncturing element after the press-on part is pressed on, a testing facility for determining at least one test parameter on which a sample-obtaining probability depends, a securing facility that, in a locked state, locks the triggering means and prevents a puncturing motion from being triggered, and, in a triggering state, releases the triggering means such that a puncturing motion can be triggered by actuation thereof. The securing facility is transitioned from the locked state to the triggering state by the testing facility when the test parameter determined by the testing facility meets defined minimum requirements. A signaling facility is provided for signaling transition of the securing facility from the locked state to the triggering state and/or for signaling that the securing facility is in the triggering state.

In this context, the sample-obtaining probability is to be understood as the probability of obtaining a useful sample by triggering a puncturing motion under the existing conditions that are characterized by the test parameter(s) determined.

An exemplary method is provided for preparing a puncturing system for generating a puncture wound for obtaining a body fluid, wherein at least one test parameter on which the sample-obtaining probability depends is being determined. It is checked whether the at least one test parameter thus determined meets defined minimum requirements and, if this is the case, a securing facility is transitioned from a locked state to a triggering state, whereby, in the triggering state, a user can trigger a puncturing motion of a puncturing element by actuating a triggering means and the triggering means, in the locked state, is locked such that no puncturing motion can be triggered, and the transition of the securing facility from the locked state to the triggering state and/or the fact that the securing facility is in the triggering state is communicated to a user by means of a signal.

It has been found that automatic triggering of the puncturing motion by a testing facility in the form of a pressure sensor, such as is the case, for example, in the puncturing system known from U.S. Pat. No. 5,879,311, is unpleasant for many users for psychological reasons and may even lead to a heightened sensation of pain. This phenomenon relates to the user of such puncturing devices having no control over the exact time of the puncture, which occurs at an indefinite time after the device is pressed against the skin. For this reason, the user usually waits for several fractions of seconds or even seconds for the puncture to occur. For many users, this waiting time is difficult to tolerate, unpleasant, and makes the puncture seem more painful.

On the other hand, the use of a pressure measuring device having a pressure range display in accordance with EP 1 360 933 is associated with a surprisingly large number of unsuccessful punctures (i.e., punctures not leading to a useful sample being obtained). On the one hand, in a device of this type, there is the risk of a puncture being triggered although the pressure range display displays that the pressure is too low, especially in the case of users with impaired vision. On the other hand, an unsuccessful puncture may occur even if the user makes sure that the pressure displayed is in order prior to actuating the triggering key. This is caused by some users reflexively moving the body part away from the press-on part upon actuation of the triggering key or at least reducing the pressure in anticipation of the puncture.

The disadvantages of the known devices can be remedied by a puncturing system according to these teachings, in that, in exemplary embodiments, the testing facility cooperates with a securing facility. If the test parameter determined by the testing facility meets defined minimum requirements, the securing facility is actuated by the testing facility such that it transitions from a locked state, in which it locks the trigger, to a triggering state, in which the trigger is unlocked such that a puncturing motion can be triggered by actuation thereof. Preferably, the transition of the securing facility is communicated to the user by an acoustic signal. In order to display that the securing facility is in the triggering state, a beeping sound, for example, can be repeated or a signal light can be turned on.

By this means it is ensured, on the one hand, that a puncture occurs only when a user actuates the triggering means. The user thus has control over the point in time at which a puncture occurs, which is of great importance for the sensation of pain for psychological reasons. On the other hand, a puncture can thus be prevented from being triggered when test parameters, such as pressure, are such that a puncture can be expected to be unsuccessful. Accordingly, a puncture occurs in a puncturing system according to these teachings only if the testing facility determines a test parameter that indicates a successful puncture can be expected and if the trigger is actuated by the user.

The test parameter determined using the testing facility of a puncturing system according to these teachings can, for example, be the pressure at which the press-on part is pressed against a body part in which a puncture wound is to be generated. Pressure sensors can, for example, contain a spring as a pressure-sensitive element. Also suitable are capacitive sensors, in which a change of the capacitance occurs as a measure of the pressure, and piezoelectric sensors. Alternatively, or in addition, the position of the body part with respect to the press-on part can also be used as test parameter. For example, the press-on part can have a relatively large opening into which the skin of a pressed-on body part, for example, a finger tip, bulges to varying extent, depending on elastic properties of the skin of the patient and handling. Another possible test parameter is the blood supply status of the body part that touches against the press-on part.

The blood supply status can be determined, for example, using an optical sensor for measurement of the blood oxygen. The measuring technology used for this purpose utilizes the spectral absorption characteristics of hemoglobin, for example, in that a beam of light having defined spectral intensities is radiated at the touching body part at two different wavelengths. The light returned from the body part is then examined, whereby conclusions regarding the hemoglobin content and thus the blood supply status of the body part can be drawn based on the different absorption at the two wavelengths. Suitable sensors are commercially available, for example, from NONIN Medical Inc., USA, and are incorporated by said company into measuring devices that are distributed under the 9500 Onyx label.

Another aspect of the invention that can be of independent significance, also for a puncturing system having no securing facility, consists of supporting a user orientating a press-on part with respect to the body part in which a puncture wound is to be generated by signals that communicate information to the user regarding the orientation of the press-on part with respect to the body part. Elderly patients, in particular, find it cumbersome to learn the correct handling of a puncturing system. In this context, many patients have problems with correctly orienting the body part, in particular, with regard to position and pressure bearing on the press-on part.

A testing facility can be used to give the user feedback in this regard such that the correct handling of the puncturing system can be made easier and quicker to learn. The testing facility preferably facilitates a visual control of the press-on part touching against the body part and/or of the body part touching against the press-on part to be made. For this purpose, for example, a camera can be integrated into the puncturing device such that a corresponding picture can be recorded and displayed by means of a display facility. A visual control can also be facilitated by means of passive optical elements, for example, minors and/or lenses instead of a camera.

The testing facility can generally support the user in orienting the press-on part with respect to the body part also by means of optical, acoustic or other signals. The press-on part can, for example, be designed such that it changes shape noticeably for the user as soon as a pressure that exceeds a predetermined minimum pressure is applied. A tactile signal can be generated in this manner.

BRIEF DESCRIPTION OF THE DRAWINGS

The above-mentioned aspects of the present invention and the manner of obtaining them will become more apparent and the invention itself will be better understood by reference to the following description of the embodiments of the invention, taken in conjunction with the accompanying drawings, wherein.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Figure 1:
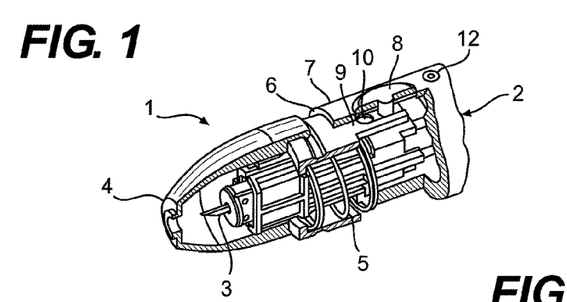
FIG. 1 is a fragmentary perspective view with portions broken away of an exemplary embodiment of a puncturing system according to the invention.

The puncturing system 1 shown in FIG. 1 comprises a puncturing device 2 and puncturing elements 3 that are intended for single use and are to be inserted in the puncturing device 2. In order to generate a puncture wound, the press-on part 4 of the puncturing device 2 is pressed against a skin surface of a user. If the pressure that is exerted in the process exceeds a minimum pressure that is defined by the strength of a spring 5, the press-on part 4 is pushed against an edge 6 of the device housing 7.

The puncturing device 2 shown has a triggering means 8 by actuation of which a user can trigger a puncturing motion after the press-on part 4 is pressed on. In the exemplary embodiment shown, the trigger or triggering means 8 is provided in the form of a button. In order to ensure that a puncture is triggered only if the puncture is expected to lead to obtaining a useful sample, the puncturing device 2 is equipped with a securing facility 9 which, in the locking or locked state shown in FIG. 1, locks the triggering means 8 such that no puncturing motion can be triggered, and, in a triggering state shown in FIG. 2, releases the triggering means 8 such that a puncturing motion can be triggered by actuation thereof.

Figure 2:
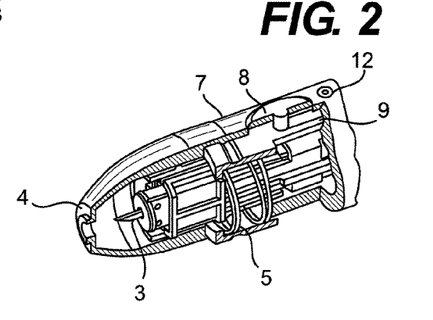
FIG. 2 shows the exemplary embodiment of FIG. 1 in an unlocked state.

In the exemplary embodiment shown, the securing facility 9 is provided in the form of a locking tongue that is attached to the press-on part 4. In the locked state shown in FIG. 1, the trigger 8 is provided as a button that is blocked mechanically by the locking tongue 9. The locking tongue 9 has a recess 10. When the press-on part 4 is pushed against the edge 6 of the device housing 7, the securing tongue 9 is also shifted with respect to the triggering button 8 until the recess 10 is flush with the triggering button 8 and thus the triggering state of the securing facility 9 that is shown in FIG. 2 is reached. In this state, the triggering button 8 is no longer blocked such that a puncturing motion can be triggered by pressing the triggering button 8.

Alternatively, the securing facility 9 can just as well be provided in the form of a switch of an electrical trigger circuit. A puncturing motion can be triggered, for example, by closing the electrical triggering circuit, whereby a first switch that is formed by the securing facility and is closed upon the press-on part 4 contacting the edge of the housing, and a second switch that is closed by actuating the triggering means 8 are disposed in the electrical circuit.

In the puncturing system shown, the user can trigger a puncture by actuating the triggering means 8 only if the pressure is sufficiently high for a puncturing motion to be expected to yield a useful sample of a body fluid. Unsuccessful punctures are avoided by a testing facility that comprises a pressure sensor in the form of a spring 5 in the exemplary embodiment shown.

The transition of the securing facility 9 from the locked state to the triggering state is displayed to the user by a suitable signal. This purpose is served by a signaling facility 12, for example, a light-emitting diode, which is used to display by means of a light signal that the securing facility 9 is in the triggering state and, consequently, a puncture can be triggered by actuating the trigger 8. Alternatively, or in addition, the signaling facility 12 can also generate an acoustic signal, for example, a beeping sound, in order to indicate the transition of the securing facility 9 to the triggering or "ready" state.

Figure 3:
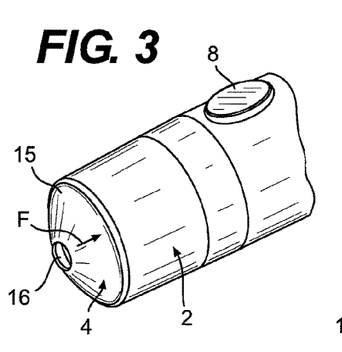
FIG. 3 is a fragmentary perspective view of another exemplary embodiment of a puncturing system according to the invention.
Figure 4:
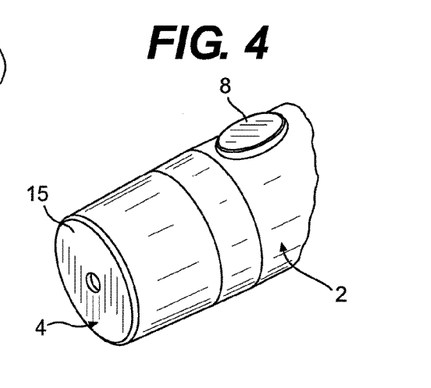
FIG. 4 shows the exemplary embodiment of FIG. 3, with the shape of the press-on part having been changed by pressure.

FIGS. 3 and 4 show another exemplary embodiment of a puncturing system, in which the testing facility of the puncturing device 2 comprises a pressure sensor in the form of a snap-action element 15 that snaps from a first configuration that is shown in FIG. 3 to a second configuration that is shown in FIG. 4 when it is exposed to a critical minimum pressure. A snap-action element of this type is a particularly advantageous pressure sensor that can be used also for puncturing systems having no securing facility, and thus is an aspect of these teachings of independent significance. The snap-action element 15 can, for example, be a metal sheet that generates an audible snapping sound when it snaps. In the first configuration shown in FIG. 3, the snap-action element 15 has a truncated cone-like shape with an opening 16, into which a skin surface of a body part touched to it can bulge.

As soon as a minimum force of, for example, 10 Newtons presses on the snap-action element 15 in the direction of the arrow F, it snaps audibly and tangibly into the second configuration shown in FIG. 4. It remains in this configuration for as long as a holding pressure is being exerted that is slightly lower than the critical minimum pressure required for snapping into the second configuration and is, for example 7 Newtons. If the holding pressure falls below this value, the snap-action element 15 snaps back to its first configuration in a spring-like fashion.

The critical minimum pressure, which when exceeded the snap-action element 15 snaps from the first configuration to the second configuration, and the holding pressure, at which, when it is not sustained, the snap-action element 15 snaps from the second configuration back to the first configuration, preferably differ by only a few Newtons, for example, 1 to 3 Newtons. The holding pressure is selected such that the conditions upon pressing the press-on part 4 against a body part at the holding pressure are such that it can be expected to be very likely that triggering a puncturing motion generates a puncture wound from which a useful sample can be obtained.

The snap-action element 15 described above is an example of a signaling facility that is integrated into the testing facility, since the snapping forth and back is used, on the one hand, to determine that the pressure detected as test parameter meets defined minimum requirements and, on the other hand, to generate an acoustic signal.

Figure 5:
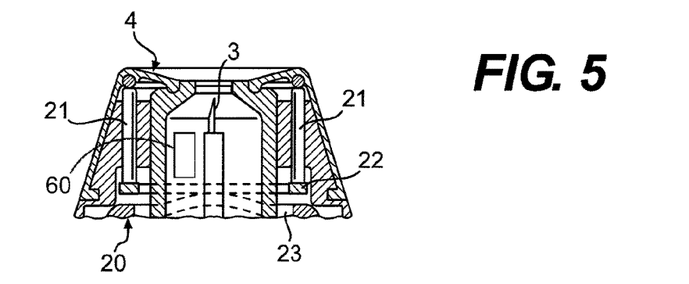
FIG. 5 is a cross-sectional view of the press-on part of another exemplary embodiment of a puncturing system according to the invention.

FIG. 5 shows a cross-sectional view of the press-on part 4 and testing facility 20 of another exemplary embodiment. The testing facility 20 of this exemplary embodiment is advantageous in that, in addition to the pressure, the orientation of the press-on part 4 with respect to the body part touching it can be checked also. For this purpose, the testing facility 20 comprises multiple (two in the exemplary embodiment shown) sensor pins 21 that are disposed such as to be mobile along their longitudinal direction. If pressure is exerted onto the press-on part 4, the sensor pins 21 are pushed against a tilt element 22 that is provided in the form of a ring in the exemplary embodiment shown. The tilt element 22 is supported on a sensor element 23 such that it tilts when the sensor pins 21 are pushed back by different distances. The sensor pressure bearing on the sensor pins 21 is transferred to the sensor element 23 only if the sensor pins 21 are pushed back by identical distances such that said sensor element 23 is pushed back against a restoring spring (not shown).

If the sensor element 23 in the testing facility described is pushed back by a critical distance that can be predetermined by the hardness of the restoring spring, this means that the pressure bearing on the sensor pins 21 is distributed essentially evenly and exceeds a critical minimum pressure.

Accordingly, the testing facility described with respect to FIG. 5 comprises a pressure sensor that can be used to determine whether or not the press-on part 4 exerts a previously defined pressure onto a skin surface and, simultaneously, whether or not the press-on part 4 is orientated such that a puncturing motion of a puncturing element 3 would proceed essentially perpendicular to said skin surface. By this means, amongst other parameters, the orientation of the press-on part 4 with respect to the body part touching it can be determined as a test parameter. If the testing facility 20 described above is connected to a display facility, a user can be supported in orienting the press-on part with respect to the body part in which a puncture wound is to be generated by means of signals that convey information to the user regarding the orientation of the press-on part 4 with respect to the body part.

The pressure sensor described with respect to FIG. 5 that can be used to render a recognition of feasible position is known from a different context, namely, for a device for needleless injection of medications, and has been described in EP 1 243 281, whose relevant content is incorporated herein by reference.

Figure 6:
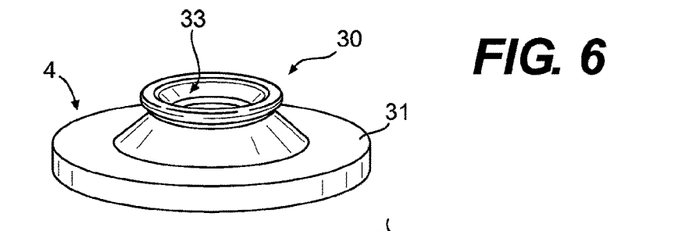
FIG. 6 is a perspective view of another exemplary embodiment of a press-on part of a puncturing system according to the invention.
Figure 7:
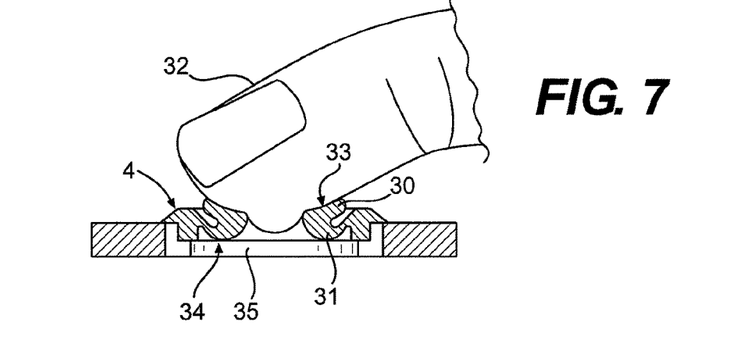
FIG. 7 shows the press-on part of FIG. 6, with a finger pressed against it.

FIGS. 6 and 7 show another exemplary embodiment of a press-on part 4 of a puncturing device. The press-on part 4 shown therein is provided as compression cone that is used to support sample collection by increasing the blood supply of the tissue at the site of injection. Suitable materials for the compression cone shown are, for example, rubber-elastic plastic materials.

The press-on part 4 has a funnel-shaped press-on ring 30 that rests on a truncated cone-shaped carrier region 31. When a body part 32 is touched to it, the internal surfaces of the press-on ring 30 nudge against the skin and effect increased blood supply to the tissue bulging into the press-on part 4. If the pressure bearing on the press-on part 4 exceeds a predetermined minimum pressure, the press-on part 4 transitions from the first configuration shown in FIG. 6 to the second configuration shown in FIG. 7 by the walls of the carrier region 31 giving way in a fashion that can be sensed by the user.

The folding-over of the press-on part 4 from the first state shown in FIG. 6 to the second state shown in FIG. 7 can be detected, for example, by an electrical contact that is closed when a suitable site 34 of the internal side of the carrier region 31 touches base ring 35. Alternatively, the deformation of the press-on part 4 can be detected just as well, for example, by means of an optical sensor. Further details and advantages of the compression cone described above are set forth in WO 01/89383, which, in this respect, is incorporated herein by reference.

Accordingly, another test parameter that is being determined in the exemplary embodiment described with regard to FIGS. 6 and 7 is whether a pressure that exceeds a predetermined minimum pressure bears on the press-on part 4. This test parameter is relevant for the sample-obtaining probability of obtaining a useful sample by triggering a puncturing motion under the existing conditions that are being characterized by the test parameter. If the predetermined minimum pressure is exceeded, it can be presumed that a puncturing motion can be used to generate a puncture wound that yields a useful sample.

Alternatively, or in addition, the testing facility can further comprise a sensor that can be used to determine the blood supply status of a body part touching against the press-on part 4 as test parameter.

The blood supply status is of great importance with regard to the question of whether a useful sample can be obtained by means of a puncturing motion with a set puncturing depth. If, for example, a finger tip is pressed against an opening of the press-on part, the skin surface bulges into the opening of the press-on part 4. This is shown schematically in FIG. 8. The blood supply status of the tissue 40 that bulges into the opening depends, amongst other factors, on the orientation of the press-on part 4 with respect to the finger and the pressure.

Figure 8:
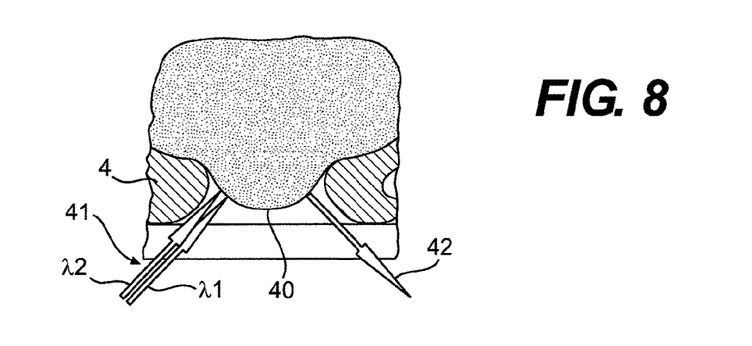
FIG. 8 is a schematic view depicting the measurement of the blood supply status of a body part pressing against the press-on part.

The measurement of the blood supply status is based on the spectral absorption characteristics of hemoglobin. Preferably, a two-wavelength measuring procedure is used, since the respective sensors can be manufactured to be very compact. In a two-wavelength measuring procedure, the tissue is irradiated with primary light 41 at the puncturing site and the spectral intensity of the returned light 42 is measured at two wavelengths $\lambda 1$, $\lambda 2$.

These two wavelengths $\lambda 1$, $\lambda 2$ are selected such that hemoglobin has a high absorption at one of the two wavelengths while the absorption of hemoglobin (and of the tissue 40) at the other wavelength is as low as possible. The ratio of the light intensities of the returned light 42 at the two wavelengths $\lambda 1$, $\lambda 2$ allows conclusions to be drawn with regard to the hemoglobin content of the tissue 40 and thus with regard to the blood supply status of the body part. It is only important in this context that the ratio of the spectral light intensities $I(\lambda 1): I(\lambda 2)$ of the primary light 41 at the two wavelengths $\lambda 1$, $\lambda 2$ is known. If necessary, this ratio can be determined by means of a separate measurement on primary light 41. However, it is preferred to use a primary light source for which the ratio of the two light intensities $I(\lambda 1): I(\lambda 2)$ is constant.

FIG. 8 schematically shows the principle of the two-wavelength measuring procedure thus described. In the primary light 41, the two wavelengths are shown by two arrows $\lambda 1$, $\lambda 2$ pointing at the tissue 40 to be examined. Light of wavelength $\lambda 1$ is strongly absorbed by hemoglobin such that spectral intensity $I(\lambda 1)$ at wavelength $\lambda 1$ in the returned light 42 is very small compared to spectral intensity $I(\lambda 2)$ at wavelength $\lambda 2$.

The ratio of the light intensities $I(\lambda 1): I(\lambda 2)$ of the returned light 42 at the two wavelengths $\lambda 1$, $\lambda 2$ can be used as test parameter in the procedure described above. By means of a comparison with a critical threshold value, it can be determined whether or not a puncture at the conditions characterized by the test parameter thus obtained would be expected to lead to obtaining a useful sample.

A particularly high user convenience is provided by puncturing systems that are used to not only generate a puncture wound, but which, in addition, comprise a sample reception unit that is used to receive a sample of a body fluid during a collection phase after a puncture. Sample reception unit 60 is shown diagrammatically in FIG. 5. Preferably, the sample reception unit is integrated into the puncturing element, for example, in that the puncturing element has a capillary channel into which body fluid penetrates during the collection phase. In puncturing systems of this type, the sample reception does not necessitate additional handling steps to be undertaken by the user. This is an important advantage, particularly for users whose dexterity is restricted by age or disease.

The puncturing device 2 preferably contains a measuring unit for examination of a sample of a body fluid thus obtained for a medically significant analyte, for example, glucose. In order to be able to obtain a useful sample for the analysis to be reliable, it is important for standardized conditions, for example, with respect to pressure and positioning of the body part on the press-on part 4, to be maintained, not only during the puncture, but also in a subsequent collection phase. The testing facility therefore preferably remains active until the end of the collection phase and displays by means of a warning signal any change of the at least one test parameter that is disadvantageous for sample reception.

In a collection phase that lasts for more than one second, a warning signal of this type gives the user the opportunity to respond to an adverse change of the test parameter such that a decreasing pressure can be elevated again or an erroneous positioning of the body part can be corrected (if required).

The testing facility may be connected to the measuring unit such that an analysis of the sample thus obtained is prevented if a critical change of a test parameter occurs during the collection phase. By this means, erroneous measuring results that may, for example, encourage a user to false insulin dosing are prevented. Another advantage of this feature is that, in measuring units that utilize for examination of a sample of a body fluid a test element that is separate from the puncturing element, the unnecessary use of a test element can be prevented.

Figures 9, 10:
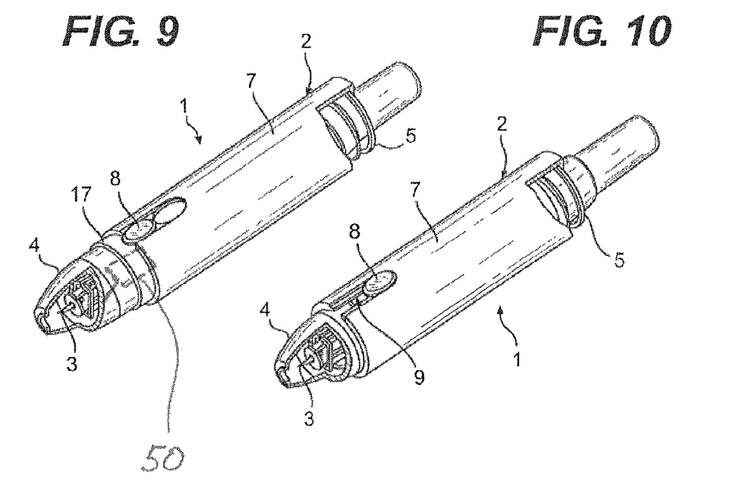
FIG. 9 is a perspective view with portions broken away of another exemplary embodiment of a puncturing system according to the invention.
FIG. 10 shows the exemplary embodiment of FIG. 9 exposed to pressure.

The structure of the puncturing system 1 shown in FIG. 9 is largely identical to that of the puncturing system described with reference to FIG. 1. It comprises a puncturing device 2 and puncturing elements 3 that are designed for single use and are inserted into the puncturing device 2. In order to generate a puncture wound, the press-on part 4 of the puncturing device 2 gets pressed onto a skin surface of a user. The press-on part 4 is shiftable with respect to a housing or housing part 7 against the spring force of a spring 5 such that the press-on part 4 proceeds from the starting position shown in FIG. 9 to an end position that is shown in FIG. 10 upon application of a predetermined minimum pressure.

The spring element 5 in this case is the pressure sensor of a testing facility that can be used to determine, as a test parameter, whether or not there bears on the press-on part 4 a pressure that exceeds a predetermined minimum pressure.

In the exemplary embodiment shown, the press-on part 4 is rigidly coupled to a puncturing element drive 50 (also referred to herein as a puncture element drive). Drive 50 and the rigid coupling to the press-on part are shown schematically in FIG. 9. Due to the rigid coupling, a set puncturing depth is not affected by a shift of the press-on part 4 with respect to the housing part 7. For this purpose, the housing part 7 is provided in the form of a bushing that surrounds an internal housing part to which belong the press-on part 4 and the puncturing element drive. The spring 5 acting between the press-on part 4 and the housing part 7 is provided in the form of a helical spring, one end of which rests on a shoulder of the housing part 7 and the other end of which is attached to the press-on part 4.

The puncturing device 2 shown has a trigger or triggering means 8 by actuation of which a user can trigger a puncturing motion after the press-on part 4 is pressed on. The triggering means 8 is provided in the form of a button that can be pressed only when it is flush with a matching recess 10 of the housing part 7. This is the case when the housing part 7 proceeded to the end position with respect to the press-on part 4, which end position is shown in FIG. 10.

In the exemplary embodiment shown in FIGS. 9 and 10, a securing facility 9 is formed by a slit that extends into the recess 10 and in which the triggering button glides into the end position shown in FIG. 10 when the press-on part is shifted. The slit 9 is so narrow that a puncture can be triggered only when the press-on part 4 is pressed to a body part at a sufficient minimum pressure.

By means of shifting the housing part 7 with respect to the press-on part 4, it can be signaled to a user by simple means, namely, in a mechanical fashion, that the puncturing device 2 is being pressed to a body part at a sufficient minimum pressure. Accordingly, it is possible to avoid resource-consuming electronic displays. In order to make it even clearer to a user that the end position shown in FIG. 10 is reached, the press-on part 4 has a visible marker 17, preferably provided as a color marker in the form of a colored ring that is visible to a user prior to the pressing-on and is covered in the end position of the press-on part 4 that is shown in FIG. 10.

The marker 17 renders it easier to distinguish between the starting position and the end position. A geometric marker, for example, a circle or a square, can be used instead of a color marker.

The marker 17 can be attached on the press-on part, as in the exemplary embodiment shown, and be covered by the housing part 7 in the end position. However, it is also feasible to provide the housing part 7 with a window with which the marker 17 interacts. Depending on the design of the device, the marker may be seen only when the press-on part 4 is in the end position or, alternatively, only when the press-on part 4 is in the starting position. However, it is feasible just as well to attach the marker on the housing part 7 and modify the press-on part 4 accordingly such that a marker attached on the housing part 7 is covered by the press-on part 4 either in the end position or in the starting position.

Figures 11, 12:
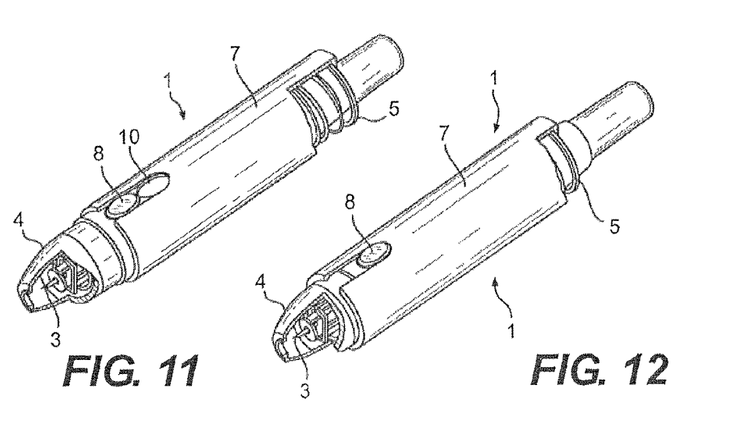
FIG. 11 is a perspective view with portions broken away of another exemplary embodiment of the puncturing system according to the invention.
FIG. 12 shows the exemplary embodiment of FIG. 11 exposed to pressure.

The advantage of simple signaling of favorable press-on conditions can also be utilized in a puncturing device 2 having no securing facility 9. FIGS. 11 and 12 show an exemplary embodiment of a puncturing system 1 that differs from the puncturing system described with respect to FIGS. 9 and 10 only in that no securing facility 9 is present. This is the case because the recess 10 of the housing part 7 in the exemplary embodiment shown in FIGS. 11 and 12 is provided in the form of a slit that is sufficiently wide that the triggering means 8 can be actuated and a puncture can be triggered with the press-on part 4 being in any position with respect to the housing part 7.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

The invention claimed is:

1. A puncturing device, comprising:
a housing;
a puncture element;
a puncture element drive disposed in the housing and adapted to move the puncture element relative to the housing in a puncturing direction;
a press-on part configured to be pressed onto a body part in which a puncture wound is to be generated and having an opening through which the puncture element extends to create the puncture wound during a puncture movement, the press-on part being rigidly connected and fixed to the puncture element drive, wherein the press-on part and the puncture element drive move together as a unit relative to the housing when the press-on part is pressed onto the body part, whereby puncturing depth of the puncture element relative to the press-on part is not affected by movement of the press-on part relative to the housing; and
a pressure sensor for determining whether pressure exerted on the press-on part meets or exceeds a defined minimum value, the pressure sensor comprising a spring element against a spring force of which the press-on part is movable relative to the housing opposite the puncturing direction.

2. The puncturing device of claim 1, further comprising a trigger which can be manually actuated to cause the puncture movement after the press-on part is pressed.

3. The puncturing device of claim 2, wherein the trigger becomes actuable when the pressure on the press-on part meets or exceeds the defined minimum value.

4. The puncturing device of claim 2, wherein the trigger is inoperable when the pressure on the press-on part is less than the defined minimum value.

5. The puncturing device of claim 4, wherein the trigger is locked when the pressure on the press-on part is less than the defined minimum value.

6. The puncturing device of claim 1, wherein the puncture element is movable in the puncturing direction only if (i) the pressure on the press-on part meets or exceeds the defined minimum value and (ii) a trigger is subsequently manually actuated.

7. The puncturing device of claim 1, further comprising a lock facility having a locked state in which the lock facility prevents the puncture element from moving in the puncturing direction.

8. The puncturing device of claim 7, wherein the lock facility further comprises a triggering state in which a puncture can take place in which the puncture element drive can be actuated.

9. The puncturing device of claim 8, wherein the lock facility is transitioned from the locked state to the triggering state when the pressure exerted on the press-on part meets or exceeds the defined minimum value.

10. The puncturing device of claim 1, further comprising a visible marker that becomes covered or uncovered when the press-on part is moved relative to the housing.

11. The puncturing device of claim 1, wherein the device signals the user regarding orientation of the press-on part with respect to the body part.

12. The puncturing device of claim 1, further comprising a signal generator that produces a signal when the press-on part meets or exceeds the defined minimum value.

13. The puncturing device of claim 1, further comprising a sample receptor configured to receive a sample of a body fluid during a collection phase after a puncture.

14. The puncturing device of claim 1, wherein the housing defines a bushing that surrounds the press-on part and the puncture element drive.

15. A puncturing device, comprising:
a housing;
a puncture element;
a puncture element drive disposed in the housing and adapted to move the puncture element relative to the housing in a puncturing direction;
a one-piece press-on part configured to be pressed onto a body part in which a puncture wound is to be generated and having an opening through which the puncture element extends to create the puncture wound during a puncture movement, the press-on part being rigidly connected and fixed to the puncture element drive, wherein the press-on part and the puncture element drive move together as a unit relative to the housing when the press-on part is pressed onto the body part, whereby puncturing depth of the puncture element relative to the press-on part is not affected by movement of the press-on part relative to the housing; and
a pressure sensor for determining whether pressure exerted on the press-on part meets or exceeds a defined minimum value, the pressure sensor comprising a spring element against a spring force of which the press-on part is movable relative to the housing opposite the puncturing direction.

16. A puncturing device, comprising:
a housing;
a puncture element;
a puncture element drive disposed in the housing and adapted to move the puncture element relative to the housing in a puncturing direction;
a press-on part configured to be pressed onto a body part in which a puncture wound is to be generated and having an opening through which the puncture element extends to create the puncture wound during a puncture movement, the press-on part being rigidly connected to the puncture element drive, wherein the press-on part and the puncture element drive move together as a unit relative to the housing when the press-on part is pressed onto the body part, whereby puncturing depth of the puncture element relative to the press-on part is not affected by movement of the press-on part relative to the housing; and
a pressure sensor for determining whether pressure exerted on the press-on part meets or exceeds a defined minimum value, the pressure sensor comprising a spring element against a spring force of which the press-on part is movable relative to the housing opposite the puncturing direction; and
a trigger which can be manually actuated to cause the puncture movement after the press-on part is pressed, the trigger being separately actuable by a user from the movement of the press-on part.

* * * * *